United States Patent [19]
Chao

[11] Patent Number: 5,688,479
[45] Date of Patent: Nov. 18, 1997

[54] PROCESS FOR REMOVING HCL FROM HYDROCARBON STREAMS

[75] Inventor: Chien C. Chao, Millwood, N.Y.

[73] Assignee: UOP, Des Plaines, Ill.

[21] Appl. No.: 628,840

[22] Filed: Apr. 5, 1996

Related U.S. Application Data

[63] Continuation-in-part of Ser. No. 362,305, Dec. 22, 1994, abandoned.

[51] Int. Cl.$^6$ ................................................. B01D 53/04
[52] U.S. Cl. .............................. 423/240 S; 423/240 R
[58] Field of Search ........................ 423/240 S, 240 R, 423/644

[56] References Cited

U.S. PATENT DOCUMENTS

| | | | |
|---|---|---|---|
| 4,639,259 | 1/1987 | Pearson | 55/71 |
| 4,673,558 | 6/1987 | Senoue et al. | 423/240 |
| 4,726,940 | 2/1988 | Kobayashi | 423/240 |
| 4,762,537 | 8/1988 | Fleming et al. | 55/71 |
| 4,786,484 | 11/1988 | Nelson | 423/239 |
| 4,792,440 | 12/1988 | Nielsen et al. | 423/244 |
| 4,861,578 | 8/1989 | Fukunaga et al. | 423/240 |
| 4,865,828 | 9/1989 | Lerner | 423/244 |
| 4,897,248 | 1/1990 | Horaguchi et al. | 423/240 |
| 5,096,680 | 3/1992 | Lindbauer et al. | 423/240 R |
| 5,173,279 | 12/1992 | Dumont et al. | 423/240 S |
| 5,316,998 | 5/1994 | Lee et al. | 502/415 |
| 5,322,674 | 6/1994 | Mori | 423/240 |

FOREIGN PATENT DOCUMENTS

| | | | |
|---|---|---|---|
| 0541329 | 5/1993 | European Pat. Off. | |
| 59-150526 | 8/1984 | Japan | 423/240 S |
| 1650224 | 5/1991 | U.S.S.R. | 423/240 S |
| 2271560 | 4/1994 | United Kingdom. | |

OTHER PUBLICATIONS

Brinker, Jeffery and Scherer, George W., "Sol–Gel Processing" *Sol–Gel Science*, Academic Press, San Diego, CA., 1990. (no month).

Germain, "Catalytic Conversion of Hydrocarbons", pp. 42, 45, & 46, 1969 (no month).

*Primary Examiner*—Ngoc-Yen Nguyen
*Attorney, Agent, or Firm*—Thomas K. McBride; John G. Tolomei; Richard P. Silverman

[57] ABSTRACT

The invention relates to a process for removing hydrogen halides from hydrocarbon containing streams. More particularly, the invention relates to a process and an HCl sorbent for the removal of HCl and other hydrogen halides from hydrocarbon streams to prevent the formation of green acids. The sorbent has a high capacity for sorption of HCl, sufficient physical strength to permit operation in packed bed form, and catalytic inertness to not causing the oligomerization reactive hydrocarbons such as olefins, diolefins. The HCl sorbent comprises an admixture of magnesium hydroxide and a hydrogen halide reactive component such as calcium hydroxide or oxide with at least one or more metal oxide, hydroxide or carbonate wherein the magnesium is present in an amount greater than about 5 mol-% of the total cation content of the sorbent.

16 Claims, No Drawings

PROCESS FOR REMOVING HCL FROM HYDROCARBON STREAMS

CROSS REFERENCE TO RELATED APPLICATIONS

This application is a continuation-in-part of application Ser. No. 08/362,305, filed Dec. 22, 1994 now abandoned and is hereby incorporated by reference.

FIELD OF THE INVENTION

The present invention relates to a method and a composition for treating hydrocarbon streams to remove acid gases. More particularly, the present invention relates to a catalytically inert sorbent for removing HCl from hydrocarbon containing streams.

BACKGROUND OF THE INVENTION

Acid gases are present as impurities in numerous industrial fluids, i.e., liquid and gas streams. These acid gases include hydrogen halides such as HCl, HF, HBr, HI and mixtures thereof. For example, one of the key processes in refining petroleum is catalytic reforming. In the catalytic reforming process, a light petroleum distillate or naphtha range material is passed over a noble metal catalyst to produce a high octane product. Hydrogen is a by-product of the catalytic reforming process, and a portion of the by-product hydrogen is recycled to the reaction zone to maintain catalyst stability. Typically, the noble metal reforming catalyst is promoted with chloride which, in the presence of hydrogen, results in the production of a small amount of hydrogen chloride. Thus, the net by-product hydrogen withdrawn from the catalytic reforming process generally contains a small amount of hydrogen chloride. Similarly, in a process for the dehydrogenation of light isoparaffins to produce isoolefins, the promoting of the noble metal catalyst with chloride will produce a net hydrogen stream containing small amounts of HCl. The net hydrogen produced in the catalytic reforming process and the dehydrogenation process is generally used in sensitive downstream catalytic processes. In addition, there are other hydrocarbon and chemical processes in which small amounts of HCl are generated and carried away in gas or liquid streams. Even small amounts of gaseous HCl present in the net hydrogen can seriously interfere with the operation of downstream processes which use the hydrogen and can cause corrosion problems in the equipment conveying the hydrogen such as pipes, valves, and compressors. Generally, HCl in gas or liquid hydrocarbon streams must be removed from such streams to prevent unwanted catalytic reactions and corrosion to process equipment. Furthermore, HCl is considered a hazardous material and releasing the HCl to the environment must be avoided.

Currently, activated alumina is the most widely used sorbent in the petroleum refining and chemical industries as a scavenger for the removal of small quantities of HCl from fluid streams. Significant developments to improve the performance of alumina to remove HCl from hydrocarbon streams are disclosed in U.S. Pat. Nos. 4,639,259 and 4,762,537 which relate to the use of alumina-based sorbents for removing HCl from gas streams. U.S. Pat. No. 5,316,998 discloses a promoted alumina sorbent for removing HCl from liquid streams by incorporating an alkali metal oxide such as sodium in excess of 5% by weight on to an activated alumina base. It is also known that alumina can be promoted to sorb more HCl by impregnating the alumina with sodium carbonate or sodium hydroxide or calcium hydroxide. The U.S. Pat. No. 4,639,259 discloses the use of calcium acetate to improve the dispersion of the calcium oxide on the alumina to achieve higher sorption capacity. The use of promoted alumina compared to other alumina-based sorbents can extend the length of time a fixed amount of sorbent will sorb HCl. By increasing the content of promoters such as sodium carbonate, or sodium hydroxide, the HCl sorption capacity of the scavenger can be increased. However, the addition of promoters to alumina to improve the capacity of the sorbent for HCL appears to have a point of diminishing returns. Despite the type and amount promoter incorporated into the alumina-based and promoted alumina materials, commercial experience shows that alumina-based and promoted alumina sorbents have a relatively low capacity for the sorption of HCl, often limited to levels less than 10–16 wt-% HCl.

Existing sorption processes for removing HCl from hydrocarbon containing streams typically involve passing the hydrocarbon containing fluid stream over the sorbent, which is disposed in a fixed bed. Conventionally, these fixed beds contain alumina-based sorbents wherein sodium or calcium is doped or coated on the alumina. Typically, the alumina-based and promoted alumina materials are formed into nodules or spheres. As the alumina-based sorbents pick up HCl, the sodium or calcium promotor, as well as aluminum, react with HCl to form chloride salts. Because HCl molecules are able to form hydrogen bonds with chloride ions, a limited amount of HCl can become physically sorbed on the surface of the salt molecules. However, the alumina sorbent in this service is known to have the undesirable property of converting certain hydrocarbons in the streams into a substance often called "green oil" which often collects in the fixed sorbent bed. Typically, these green oils are green or red in color. They generally contain chlorinated $C_6$–$C_{18}$ hydrocarbons and are believed to be oligomers of light olefinic hydrocarbons. The presence of green oils in the fixed sorbent bed fouls the sorbent bed and results in the premature failure of the sorbent. When this fouling occurs, often costly measures are required to remove the spent sorbent from the bed. Furthermore, the chloride content of the green oils on the spent sorbent makes disposal of the spent sorbent an environmental problem. While the exact mechanism of green oil formation is unknown, it is believed that green oils are formed by catalytic reaction of aluminum chloride or HCl with the hydrocarbon resulting in a chlorinated hydrocarbon. Since both aluminum chloride and free HCl are known to be acidic and present on the surface of the sorbent, they are able to catalyze the polymerization of reactive hydrocarbons. Since it is very difficult to avoid the physical sorption of HCl and the formation of chloride salts on alumina-based and promoted alumina sorbents, the catalyzed polymerization reaction of hydrocarbon and the formation of green oil is not easily avoided. Green oil formation remains an unresolved industry problem during the removal of HCl from hydrocarbon streams.

Typically, acid gases such as hydrogen halides found in flue gases as combustion products of streams containing chlorinated compounds. To minimize the emissions of these compounds which have been linked to acid rain and smog, alkaline sorption agents—particularly those selected from among oxides and hydroxides of calcium, magnesium, and the alkali metals—are conventionally employed to remove acid gases from flue gases. U.S. Pat. No. 4,792,440 to Nielson, which discloses a process for purification of flue gases by the addition of a dry alkaline sorption agent to the flue gas, is representative of such a process. In a similar process, U.S. Pat. No. 4,897,248 to Horaguchi et al. discloses a method for treating an exhaust gas containing HCl by blowing an alkaline neutralizing agent in the form of a cooled powder to remove the HCl, recovering the used powder, cooling the used powder, and returning it again to treat the exhaust gas. Flue gases, combustion gases, and exhaust gases are very different from hydrocarbon fluid streams containing impurities such as acid gases like HCl. Generally, exhaust gases contain very small amounts of hydrocarbons and there are no reactive hydrocarbons present that would result in the formation of green oil. Furthermore, flue and exhaust gases represent very large volumes of gas at low pressure and at high temperature. Such a combination would not normally suggest the use of a fixed sorbent bed for the removal of acid gas, and therefore many flue gas treatment systems employ sorbents in powder form which are injected directly into the flue gas stream.

The fabrication of semiconductor devices typically involves the etching of various surfaces with strong acids which result in the production of dry waste gases comprising gases such as HF and HCl. U.S. Pat. No. 5,322,674 discloses a method of removing HCl from such waste gases by contacting the gases first with activated carbon and then contacting the effluent with either calcium hydroxide or ferric oxide. U.S. Pat. No. 4,673,558 relates to a similar process for treating chloride containing waste gas with magnesium oxide particles. U.S. Pat. No. 4,861,578 discloses treating such a waste gas in a compound bed wherein the waste gas is first contacted with a magnesium compound and subsequently contacted with a calcium compound wherein the alkali compounds are hydroxides, oxides, carbonates, and mixtures thereof.

When unsaturated hydrocarbons such as butadiene or other olefinic compounds are present in a hydrocarbon containing stream, these compounds can be polymerized on acidic surfaces. Alumina based sorbents and promoted alumina sorbents for sorbing HCl become acidic during the sorption process, and thus, acquire catalytic activity which results in the polymerization of reactive hydrocarbons in the stream; and the formation of these polymers foul the sorbers, shorten sorbent life, and create a disposal problem. Since an HCl sorbent is not regenerable, the treatment of streams with even moderate to high HCl content, such as an HCl sorbent with a capacity of 10–16 wt-% requires the fixed bed of sorbent to be changed frequently and imposes a downtime on the upstream process. When the change of sorbent requires costly measures to dig the sorbent out of the sorbent bed, the loss of production and the maintenance costs can become even more significant. When green oils are produced during the HCl sorption process, the spent sorbent represents a costly disposal problem.

It is an objective of the present invention to discover an HCl sorbent which is catalytically inert to reaction of hydrocarbons and the formation of green oils.

It is an objective of the present invention to discover an sorbent for HCl from hydrocarbon containing stream with a higher capacity for sorption of HCl with a minimum requirement for maintenance costs.

It is objective of this present invention to seek an sorbent which does not result in the production of potentially hazardous chlorinated hydrocarbons.

SUMMARY OF THE INVENTION

The present invention is directed to methods for the sorption of HCl and other halogen halides from fluid streams which contain hydrocarbons. The sorbents of the present invention exhibit a low catalytic activity for hydrocarbon polymerization, a high HCl sorption capacity, and good physical strength when in aggregated form. Since the physical sorption of HCl is generally thought to be a surface phenomenon, and the presence of HCl on the surface of the sorbent would tend to catalyze the polymerization of hydrocarbon, it is surprising that the HCl sorbents of the present invention show such a low catalytic activity. Surprisingly, the magnesium bonded sorbents had much lower catalytic activity than alumina based or alumina promoted sorbents and a much higher overall sorption capacity than the adsorbents of the prior art. According to the present invention, a process is provided for treating a hydrocarbon stream or hydrocarbon containing fluid stream comprising hydrogen, hydrocarbons, water, and a hydrogen halide. In order to remove the hydrogen halide from the fluid stream, the fluid stream is contacted with a sorbent comprising an admixture of magnesium hydroxide and a hydrogen halide reactive material is selected from the group consisting of an oxide, hydroxide, or carbonate of an alkali metal or an alkaline earth metal to form a cross-linked aggregate when calcined at a temperature below about 580° C. Preferably, the sorbent of the present invention is formed into pellets or beads with a high surface area or a renewable surface.

In another embodiment, the invention relates to an HCl sorbent for removing HCl from hydrocarbon containing streams. The HCl sorbent comprises a mixture of magnesium compound such as the oxide or the hydroxide with at least one or more metal oxides, hydroxide or carbonate wherein the metal is selected from the group consisting of magnesium, calcium, strontium, barium, sodium and potassium. Following calcination at a temperature of less than about 580° C. for a time period less than about 1 hour, the aggregate is characterized as cross-linked. The aggregate has an average pore radius of about 100 Å to about 100000 Å, a surface area ranging from about 20 $m^2$/gm to about 600 $m^2$/gm. Preferably, the aggregate comprises magnesium in an amount greater than about 5 mol-% of the total cation content of the sorbent.

DETAILED DESCRIPTION OF THE INVENTION

There are many compounds that are reactive to acid gases such as hydrogen halides which can be employed as a scavenger sorbent to remove trace amounts of acid gases from fluid streams. However, for a compound to function in a fluid stream from a process plant where hydrocarbons are present, the material must have good acid gas sorption capacity, have sufficient physical strength, and be catalytically inert in the presence of reactive hydrocarbons.

Good acid gas sorption capacity means that the sorbent material should have a high surface area such that the reactive molecules of the sorbent are at the surface where they can be reached and readily react with the acid gas. Alternately, the surface of the sorbent can renew itself readily such that the accessibility of the sorbent molecules at the surface is not limited to the original surface layer. On reaction of the acid gas with the reactive agent, such as $Ca(OH)_2$, it is believed that the salt formed detaches from the surface and establishes a new crystal, thereby exposing a new layer of active reactive agent. The new salt crystal structure will reside in the void space of the macro pore structure of the sorbent. Preferably, the sorbent of the present invention will have void space of about 0.05 cc/gm to about 0.5 cc/gm, and more preferably, a void space from about 0.2 to 0.5 cc/gm. Preferably, for removing HCl from hydrocarbon streams, the acid gas sorption capacity of the preferred acid gas sorbent will be about 15 to about 50 wt-% HCl, more preferably, the HCl sorption capacity will be greater than 20 wt-% HCl, wherein the HCl sorption capacity is measured by any suitable means. By sufficient physical strength it is meant that the sorbent must be formed in a physical shape and size which allows a sufficient amount of fluid to flow through a packed bed of the sorbent without causing an excessive pressure drop, and the sorbent must have sufficient physical strength to withstand the weight of a packed bed. Catalytically inert means that even after HCl sorption, the HCl loaded sorbent will not cause dimerization or oligomerization of reactive hydrocarbons such as hexene or 1,3 butadiene.

The composition of the sorbent of the present invention consists of a binder and a hydrogen halide reactive agent. The preferred composition of the sorbent comprises magnesium hydroxide and a hydrogen halide reactive material which is very reactive towards an acid gas such as hydrogen chloride. The hydrogen halide reactive material is selected from the group consisting of calcium hydroxide, calcium oxide, calcium carbonate, magnesium carbonate, strontium hydroxide, barium hydroxide, sodium hydroxide, sodium carbonate, sodium bicarbonate, potassium carbonate, potassium hydroxide, potassium bicarbonate and mixtures thereof. More preferably the sorbent composition of the present invention comprises an admixture consisting of magnesium hydroxide and the hydrogen halide reactive material. Most preferably, the sorbent composition of the present invention comprises an admixture consisting essentially of magnesium hydroxide and a hydrogen halide reactive material such as calcium hydroxide, calcium oxide, calcium carbonate, and mixtures thereof. With magnesium hydroxide in the admixture, and the admixture is calcined at a temperature below about 580° C., the formation of an sorbent aggregate results from a condensation reaction of the magnesium hydroxide by a process known as olation. Olation is a condensation process in which an hydroxy bridge is formed between two metal centers followed by dehydration to complete the cross-linking. A detailed mechanism of the reaction is described in a text entitled, *SOL-GEL Science*, by C. Jeffery Brinker and George W. Scherer, Academic Press, Inc., 1990, on pages 26–27 and page 546 which are hereby incorporated by reference. Such an olation reaction is illustrated below as water is removed from the two metal centers to provide the cross-linked structure:

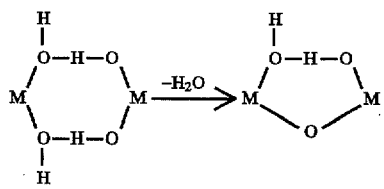

The calcination of the sorbent admixtures of the present invention preferably is carried out at a temperature below 580° C. and more preferably is carried out at a temperature range of between about 300° C. to about 450° C. At these conditions, it is believed that a portion of the magnesium hydroxide dehydrates forming magnesium oxide by cross-linking with the hydrogen halide reactive agent. This cross-linking provides the macro porosity of the sorbent, as well as a structural backbone to provide physical strength to the sorbent. Magnesium oxide is not very reactive to HCl; therefore, it is possible for magnesium oxide in this cross-linked form to serve as the backbone of an sorbent to provide the physical strength for the sorbent of the present invention throughout its life span. In a less preferred design, one can use a neutral material or, an inert material such as silica as an additional binder in the sorbent admixture.

The hydrogen halide reactive agent can be selected from a large array of compounds classified as basic such as sodium hydroxide, potassium hydroxide, calcium hydroxide, strontium hydroxide, barium hydroxide, calcium oxide, strontium oxide, sodium carbonate, potassium carbonate, calcium carbonate, and mixtures thereof. Magnesium hydroxide, and its related compounds such as magnesium oxide and magnesium carbonate also can serve as the reactive agent. However, some hydrogen halide reactive agents are better than the others for a number of reasons. Calcium hydroxide is preferred for its ability to cross-link with magnesium hydroxide. The product of the olation or condensation reaction for magnesium hydroxide is magnesium oxide. Other hydrogen halide reactive agents such as sodium hydroxide and potassium hydroxide do not form a free powder easily, this produces powders which are less convenient to employ in the formation of aggregates by the bonding or the cross-linking process. Sodium carbonate, which has good water solubility, tends to form relatively weak aggregates.

When magnesium hydroxide is employed as the binder for the sorbent, MgO which is formed during calcination and cross-linking process. Magnesium oxide is less reactive to HCl than the magnesium hydroxide. To illustrate the relative hydrogen halide sorbent capacity of individual compounds such as $Ca(OH)_2$, $CaCO_3$, $CaO$, $Mg(OH)_2$, $MgCO_3$, and $MgO$, samples of these compounds in powder form were exposed to a gas comprising HCl and after a time, the extent of reaction was measured. It was found that $Ca(OH)_2$ sorbed 55.9 wt % HCl, and MgO sorbed about 9.5 wt-% HCl.

It was surprisingly discovered that an sorbent which has a much higher HCl sorption capacity than pure $Ca(OH)_2$ can be prepared by combining the calcium hydroxide with magnesium hydroxide to provide the sorbent of the present invention. This synergism was observed on samples prepared by precipitating calcium and magnesium hydroxide from a mixed salt solution by adding sodium hydroxide. It was shown that a sample prepared by adding NaOH solution into a mixed solution of 1M $CaCl_2$ and 1M $MgCl_2$ resulted in a 90% HCl sorption capacity. A second sample made by adding NaOH into a mixed solution of 1M $CaCl_2$ and 2M $MgCl_2$ gave 93% HCl sorption capacity. Both samples exhibited a greater acid gas sorption capacity for HCl than that measured for pure calcium hydroxide.

Sorption aggregates of the present invention may be produced by physically mixing calcium hydroxide and magnesium hydroxide powders followed by extrusion and calcination. The calcination step is preferably carried out at a temperature above about 300° C. and below about 580° C., and more preferably the calcination step is carried out at a temperature ranging from about 300° C. to about 450° C. Following the calcination step at these conditions, the magnesium hydroxide component is at least partially converted to magnesium oxide in the calcination step and becomes relatively inert. Because the calcium hydroxide is known to dehydrate at temperatures above 580° C., the calcium hydroxide that is bound in the aggregate structure is not changed and its strong reactivity to acid gases such as HCl is retained.

The total magnesium cation content present in the magnesium compound as either magnesium hydroxide or magnesium oxide in the sorbent aggregate is preferably greater than about 5 mol-%; otherwise, after HCl sorption, the sorbent may lack sufficient physical strength for commercial application in fixed beds. The preferred amount of magnesium cation content of the sorbent of the present invention comprises between 5 and 50 mol-% magnesium cation, and the more preferred composition is about 15 mol-% $Mg(OH)_2$ and about 85 mol-% $Ca(OH)_2$. As it will be shown in the examples, this composition has higher HCl sorption capacity than its magnesium-rich counterparts. As the examples show for HCl sorption, all of the sorbent aggregates of the present invention have much higher hydrogen halide capacity than the modified alumina sorbent.

A portion of the capacity of the sorbent for sorbing HCl results from the reaction of the sorbent with HCl. The reaction products of HCl and the sorbent are salts such as calcium chloride and magnesium chloride. These salts are substantially neutral compounds and do not contribute any catalytic activity to reactions of hydrocarbons or organics with the hydrogen halide in the fluids. However, these salts are still able to physically sorb HCl by hydrogen bonding, and thus an HCl loaded sorbent could still promote catalytic activity for polymerization of hydrocarbons.

To measure the catalytic reactivity of the sorbent for hydrocarbons, 1-hexene was used as the reactant. The sorbent was first loaded with HCl by exposing the sorbent to HCl gases. The unsorbed HCl was removed and the now HCl loaded sorbent was exposed to 1-hexene. For those sorbents that are not catalytically active, 1-hexene was only physically sorbed. For catalytically active sorbents, the sorption of 1-hexene resulted in the production of $C_{12}$ or larger molecules. These heavy molecules formed a liquid phase (not sorbed) on the surface of solid sorbent. Surprisingly, the magnesium bonded sorbents had much lower catalytic activity than alumina based or alumina promoted sorbents.

Preferably, the sorbents of the present invention comprise a surface area of about 20 to 600 $m^2/gm$. It was discovered that while most of the HCl sorption occurred at the surface of the sorbent particle and that the available surface area of the sorbent tested typically ranged from about 50 to 100 $m^2/gm$, the available surface area did not account for the very large HCl loadings observed. Therefore, it is believed that some of the reactive agents in the sorbent becomes available for reacting with acid gases by surface renewal.

EXAMPLES

To more fully illustrate the invention, the following examples are presented.

Example I

Samples of sorbent materials considered to be reactive to HCl were evaluated to determine an equilibrium loading of HCl on the sorbent material. Approximately 3 gms of each sorbent material, as a compressed powder were placed in a conventional McBain Bakker Balance. A detailed description of this device in general can be found in text books such as "Physical Adsorption of Gases" by D. M. Young and A. D. Crowell, Butterworths, 1962. The sorbent materials evaluated included calcium hydroxide, calcium oxide, calcium carbonate, magnesium hydroxide, magnesium oxide, and magnesium carbonate. The results of this reactivity survey are shown in Table 1. The sorbents were first activated at temperatures ranging from about 97° C. to about 207° C. such that no structure change of the materials took place and then sorption was carried out with a gas containing HCl having a partial pressure of HCl of about 120 torr. HCl sorption during the test procedure was monitored by the balance and the final sorbent loadings were determined by chemical analysis of the spent samples. Table 1 presents the results of the chemical analysis. The results revealed that among the compounds tested, calcium hydroxide had the highest HCl sorption capacity. Depending on the activation temperature of the sample, calcium hydroxide sorbed HCl at capacities from to 35.9 to 55.9 wt % of its own weight, showing calcium hydroxide to be a strong reactive agent. Magnesium hydroxide ranked second in sorbing from about 26.9 to 27.4 wt % HCl showing magnesium hydroxide to be a moderately strong reactive agent. The HCl capacities of metal oxides were lower than for the metal hydroxides. For example, CaO sorbed 16.1 wt % and MgO sorbed 9.5 wt % HCl. Calcium carbonate sorbed 12.8 wt % and magnesium carbonate sorbed 22.8 wt % HCl.

TABLE 1

| McBAIN HCl ADSORPTION CAPACITIES | | | |
|---|---|---|---|
| SAMPLE NAME | ACTIVATION TEMPERATURE | ADSORPTION TEMPERATURE | HCl 119 torr 41 hr wt % |
| $Mg(OH)_2$ | 108° C. | 22° C. | 26.9 |
| $Mg(OH)_2$ | 216° C. | 22° C. | 27.4 |
| MgO | 208° C. | 22° C. | 9.5 |
| MgCO3 | 204° C. | 22° C. | 22.8 |
| Ca(OH)2 | 97° C. | 22° C. | 35.9 |
| Ca(OH)2 | 197° C. | 22° C. | 55.9 |
| CaO | 203° C. | 22° C. | 16.1 |
| CaCO3 | 207° C. | 22° C. | 12.5 |

Example II

A sorbent aggregate with a 50/50 molar ratio of calcium to magnesium was prepared by dissolving 101.6 grams of $MgCl_2$—$6H_2O$ and 73.5 grams of $CaCl_2$—$2H_2O$ in 1 liter of distilled water. 160 grams of a 50% NaOH solution was added to the solution at room temperature with vigorous stirring. The resulting solid precipitate was filtered and washed with water and dried under nitrogen. The 50/50 precipitate aggregate powder is referred to as $Ca_{0.5}Mg_{0.5}(OH)_2$.

A sorbent aggregate with a 33/66 molar ratio of calcium to magnesium was prepared by dissolving 203.2 grams of $MgCl_2$—$6H_2O$ and 73.5 gm of $CaCl_2$—$2H_2O$ in 1 liter of water. 240 grams of a 50% NaOH solution was added to the salt solution at room temperature with vigorous stirring. The resulting solid precipitate was filtered, washed with water, and dried under nitrogen. The 53/67 precipitate is referred to as $Ca_{0.33}Mg_{0.66}(OH)_2$.

Both the 50/50 and the 33/66 samples were vacuum activated at 350 C and tested in McBain balance. After exposure to a gas having an HCl partial pressure of 100 torr for a period of 48 hours, $Ca_{0.5}Mg_{0.5}(OH)_2$. sorbed 90.4 wt % HCl, and $Ca_{0.33}Mg_{0.66}(OH)_2$. sorbed 93.1 wt % HCl.

Example III

The HCl capacities of a number of commercially available alumina-based materials were measured in the McBain Bakker balance for HCl sorption at about 100 torr. for a period of 5 days. The HCl loadings for these alumina materials reached a maximum loading ranging from about 9.7 to about 16 wt-% as shown in Table 2. The HCl sorption capacities of the alumina-based and promoted alumina sorbents are far less than that of calcium hydroxide as shown in Table 1, and less than the calcium and magnesium mixed oxide sorbent aggregates of Example II. At conditions similar to the experiment in Example II, activated alumina, A, showed the lowest HCl sorption capacity at 9.7 wt-% HCl and the sodium promoted alumina, G, activated at 364° C., showed the highest alumina HCl sorption capacity at 15.8 wt-%.

After vacuum activation at 367° C., the uncalcined pellets showed an HCl sorption capacity of about 24.36 wt-% HCl following exposure to an 88 torr HCl containing gas for a period of about 96 hours at a sorption temperature of 22° C.

TABLE 2

McBAIN HCl ADSORPTION OVER ALUMINA

|   |   | McBAIN ACT. TEMPERATURE | ADSORPTION TEMPERATURE | HCl 100 TORR 5 DAYS IN WT % |
| --- | --- | --- | --- | --- |
| A | ACTIVATED ALUMINA | 344° C. | 22° C. | 9.70 |
| B | Na PROMOTED ALUMINA | 343° C. | 22° C. | 10.00 |
| C | Na PROMOTED ALUMINA | 346° C. | 22° C. | 13.38 |
| D | Ca PROMOTED ALUMINA | 346° C. | 22° C. | 12.23 |
| E | Na PROMOTED ALUMINA | 347° C. | 22° C. | 13.69 |
| F | Na PROMOTED ALUMINA | 347° C. | 22° C. | 11.10 |
| G | Na PROMOTED ALUMINA | 364° C. | 22° C. | 15.78 |

Example IV

Approximately 3000 grams of magnesium hydroxide powder was placed in a muller and about 1100 ml of distilled water was added. The mixture was mulled for about ½ hour, until a homogeneous dough was obtained. The dough was extruded to provide a 0.3175 cm (⅛ inch) cylindrical extrudate pellets. About 225 grams of pellets were placed in an oven with an air purge and were calcined according to the following heating sequence: 1 hour from ambient temperature to about 200° C.; 2 hours at 200° C.; 30 minutes from 200° to 300° C.; 30 minutes from 300° C. to 400° C., and 1 hour at 400° C. The calcined pellets were placed in a dry container to prevent reaction with carbon dioxide in the air. A mercury porsimetry test indicated the calcined pellets had a pore volume of 0.57 ml/gm and a total pore area of 152 sqm/gm. In a McBain Bakker test activated at about 381° C. for sorption of HCl as described in Example I, the calcined magnesium hydroxide pellets reached an HCl sorption capacity of about 28.5 wt-% after being exposed to HCl at 105 torr for about 23 hours at an sorption temperature of 22° C. Clearly this material, which represents an sorbent aggregate comprising magnesium oxide and magnesium hydroxide, has a much higher HCl sorption capacity than alumina sorbents in Example III.

Example V

A mixture of 87.5 grams of magnesium hydroxide and 22.2 grams of calcium hydroxide was placed in a 1 liter bottle and shaken in a paint shaker for about 10 minutes. The mixture was them placed in a Hobart mixer with a sufficient amount distilled water to create an extrudable dough. As in Example IV, the dough was extruded to provide 0.3175 cm (⅛ inch) extrudate pellets. About 15 grams of pellets were flash calcined in a calcination tube. The calcination tube comprised a 1-inch diameter quartz tube and was divided into a sample zone and a preheating zone, packed with quartz chips. The preheating zone and the sample zone were placed in a vertical mounted tube furnace and maintained at 650° C. with an air purge rate of about 600 cc/min. Wet pellets were dropped into the quartz tube and retained in the tube furnace for about 10 minutes. The calcined pellets formed an aggregate with a 17/83 mole ratio of calcium hydroxide to magnesium oxide.

Similarly, following activation at about 401° C., the 17/83 flash calcined pellets sorbed about 27.07 wt-% HCl. These materials had a much higher HCl sorption capacity than alumina sorbents in Example III.

Example VI

According to the procedure of Example IV, 105 grams of magnesium hydroxide and 44.5 grams of calcium hydroxide were prepared to provide uncalcined and flash calcined 0.3175 cm (⅛ inch) pellets having a 25/75 molar ratio of magnesium to calcium. Measured HCl sorption capacity for the uncalcined and flash calcined pellets was 26 wt-% HCl and 29.01 wt-% HCl following activation temperature of 356° C. and 388° C., respectively. These materials had much higher HCl sorption capacity than the alumina sorbents in Example III.

Examples VII

A 0.3175 cm (⅛ inch) pellet having a 50/50 molar ratio of magnesium to calcium was prepared with 1704.3 grams of calcium hydroxide and 1341.5 grams of magnesium hydroxide according to the procedure of Example IV. The dough was extruded into 0.3175 cm pellets and a portion of the extrudate pellets was calcined in air as the temperature was raised from ambient temperature to about 400° C. over a 1 hour period, and then was maintained at 400° C. for 1 hour. The 50/50 aggregate pellets were placed in a dry container to cool. The uncalcined and calcined 50/50 aggregate showed an HCl sorption capacity at 22° C. of 28.15 and 30.01 wt-% HCl, respectively, after 24 hours exposure to a gas having an HCl partial pressure of about 105 torr. The McBain Bakker activation temperature for the uncalcined and calcined samples was 370° C. and 389° C., respectively. These 50/50 aggregate materials had a much higher HCl sorption capacity than alumina sorbents in Example III.

Example VIII

An aggregate with a 15/85 molar ratio of magnesium to calcium was prepared with 2000 grams of calcium hydroxide and 253.5 grams of magnesium hydroxide according to the procedure of Example IV to form uncalcined pellets. The measured mercury porimetry of the pellets indicated a pore volume of 0.35 ml/gm and a pore area of 53.9 sq-m/gm. The uncalcined pellets, following activation at 406° C., sorbed 43.02 wt-% HCl after exposure to HCl for 24 hours at 87 torr. The 400° C. calcined 15/85 pellets sorbed about 23.93 wt-% HCl after 24 hours at 87 torr in the McBain Bakker device. These materials had a much higher HCl sorption capacity than alumina sorbents in Example III.

Example IX

The HCl loaded sorbents of Example I were subjected to a further test to evaluate the catalytic reactivity of the HCl loaded sorbent material to hydrocarbons. Following HCl sorption experiments in Example I, the McBain system was evacuated briefly to remove all residual HCl gas. The samples were then exposed to a gas comprising 1-hexene at a partial pressure of about 50 torr. For those sorbents which were not catalytically active, the 1-hexene was sorbed, rapidly reaching an sorption equilibrium state after which point the weight of sorbed material did not increase with time. However, on catalytically active sorbent materials, the 1-hexene continued to react to form oligomers. The oligomerization reaction did not reach equilibrium, as evidenced by the continued weight gain with exposure time. The results of 1-hexene sorption of sorbents in Example I are shown in Table 3.

Similar 1-hexene sorption experiments were conducted on HCl loaded alumina samples, including, activated alumina, sodium promoted alumina, and calcium promoted alumina. The results of 1-hexane sorption on alumina samples also are shown in Table 3.

All of the calcium and magnesium sorbent aggregate materials showed very low weight gains and those weight gains stopped very rapidly. In comparison, the weight gains of activated alumina material were large and the weight gains continued at steady pace throughout the experimental period. Clearly the magnesium and calcium materials had a lower catalytic activity than the alumina-based materials.

TABLE 3

| | | HEXENE OLIGOMER FORMATION | | |
|---|---|---|---|---|
| SORBENT MATERIAL | ACTIVATION TEMPERATURE | ADSORPTION TEMPERATURE | 1-HEXENE | |
| | | | 57 TORR 21 HRS | 57 TORR 120 HRS |
| Mg(OH)2 | 108° C. | 22° C. | 1.04 | 1.11 |
| Mg(OH)2 | 216° C. | 22° C. | 0.94 | 1.05 |
| MgO | 208° C. | 22° C. | 0.65 | 0.78 |
| MgCO3 | 204° C. | 22° C. | 0.61 | 0.74 |
| Ca(OH)2 | 97° C. | 22° C. | 0.14 | 0.05 |
| Ca(OH)2 | 197° C. | 22° C. | 0.03 | −0.06 |
| CaO | 203° C. | 22° C. | 0.07 | 0.18 |
| CaCO3 | 207° C. | 22° C. | −0.05 | 0.00 |
| | | | 54 TORR 22 HRS | 45 TORR 5 DAYS |
| A-Activated Alumina | 344° C. | 22° C. | 14.50 | 18.72 |
| B-Na Promoted Alumina | 343° C. | 22° C. | 12.19 | 12.91 |
| C-Na Promoted Alumina | 346° C. | 22° C. | 8.93 | 10.17 |
| D-Ca Promoted Alumina | 346° C. | 22° C. | 17.81 | 28.42 |
| E-Na Promoted Alumina | 347° C. | 22° C. | 14.37 | 15.31 |
| F-Na Promoted Alumina | 347° C. | 22° C. | 22.90 | 31.89 |
| G-Na Promoted Alumina | 364° C. | 22° C. | 11.34 | 13.98 |

Example X

Portions of the 15/85 calcined pellets of Example VIII were dried at 100° C., 200° C., 300° C. and 400° C. and placed individually in the McBain Bakker device to access catalytic activity according to the procedures in Example IX. The results of the hexene-1 oligomerization formation of these four sorbents, as well as three promoted alumina sorbent, are shown in Table 4. The catalytic activity 15/85 Mg/Ca sorbents was essentially nil and well below that of the aluminum-based sorbents.

TABLE 4

| | 1-HEXENE OLIGOMER FORMATION ON HCl LOADED 15/85 AGGREGATE | | | | | |
|---|---|---|---|---|---|---|
| | | ACTIVATION | ADSORPTION | 1-HEXENE AT 57 TORR | | |
| SAMPLE | DRYING TEMPERATURE | TEMP., °C. | TEMP., °C. | 22 HRS | 240 HRS | Δ |
| A | 100° C. | 60 | 22 | .38 | .40 | 0.02 |
| B | 200° | 120 | 22 | .41 | .49 | 0.08 |
| C | 300° C. | 275 | 22 | .19 | −.37 | −0.56 |
| D | 400° C. | 360 | 22 | 1.24 | 1.34 | 0.10 |

We claim:

1. A process for the removal of hydrogen halide from a fluid hydrocarbon stream comprising hydrogen, hydrocarbons, water and hydrogen halide, which process comprises contacting said stream with a sorbent material in a packed bed, said sorbent material being catalytically inert to formation of green oils from said hydrocarbons, said sorbent material comprising an admixture of magnesium hydroxide and a hydrogen halide reactive material selected from the group consisting of calcium hydroxide, calcium oxide, strontium hydroxide, barium hydroxide, sodium hydroxide, potassium hydroxide, and mixtures thereof, wherein said admixture is calcined at a temperature above about 300° and below about 580° C. to form a cross-linked sorbent material.

2. The process of claim 1 wherein magnesium comprises greater than about 5 mol. % of the total cation content of said sorbent material.

3. The process of claim 1 wherein said hydrogen halide is selected from the group consisting of hydrogen chloride, hydrogen fluoride, hydrogen iodide, hydrogen bromide and mixtures thereof.

4. The process of claim 1 wherein said hydrogen halide reactive material is selected from the group consisting of calcium hydroxide and calcium oxide.

5. The process of claim 1 wherein said stream comprises a net hydrogen stream from a catalytic reforming process and said hydrogen halide is hydrogen chloride.

6. The process of claim 1 wherein said stream comprises a net hydrogen stream from a light paraffin dehydrogenation process and said hydrogen halide is hydrogen chloride.

7. The process of claim 1 wherein said sorbent material has a surface area ranging from about 20 to about 600 $m^2/gm$.

8. The process of claim 1 wherein said hydrogen halide reactive material is calcium hydroxide and said sorbent material comprises from about 5 to 50 mol % of magnesium compound.

9. The process of claim 8 wherein said sorbent material comprises about 15 mol % of magnesium compound and about 85 mol % of calcium hydroxide.

10. The process of claim 1 wherein said admixture is calcined at a temperature ranging from about 300° to about 450° C.

11. The process of claim 1 wherein said admixture includes a binder comprising a neutral material.

12. The process of claim 11 wherein said neutral material comprises silica.

13. A process for the removal of hydrogen halide from a liquid hydrocarbon stream comprising hydrogen, hydrocarbons, water and hydrogen halide, which process comprises contacting said stream with a sorbent material in a packed bed, said sorbent material being catalytically inert to formation of green oils from said hydrocarbon, said sorbent material consisting of an admixture of magnesium hydroxide and a hydrogen halide reactive material selected from the group consisting of calcium hydroxide, calcium oxide, strontium hydroxide, barium hydroxide, sodium hydroxide potassium hydroxide, and mixtures thereof, wherein said admixture is calcined at a temperature above about 300° and below about 580° C. to form a cross-linked sorbent material.

14. A process for the removal of hydrogen halide from a hydrogen stream comprising hydrogen, hydrocarbons, water and hydrogen halide, which process comprises contacting said stream with a sorbent material in a packed bed, said sorbent material being inert to reaction of the hydrocarbons to the formation of green oils, said sorbent material consisting of an admixture of magnesium hydroxide and a hydrogen halide reactive material selected from the group consisting of calcium hydroxide, calcium oxide, and mixtures thereof, wherein said admixture is calcined at a temperature between about 300° and about 580° C. to form a cross-linked sorbent material.

15. The process of claim 14 wherein said stream comprises a net hydrogen stream from a catalytic reforming process and said hydrogen halide comprises hydrogen chloride.

16. The process of claim 14 wherein said stream comprises a net hydrogen stream from a light paraffin dehydrogenation process and said hydrogen halide comprises hydrogen chloride.

* * * * *